(12) United States Patent
Ridker et al.

(10) Patent No.: US 8,101,363 B2
(45) Date of Patent: Jan. 24, 2012

(54) INFLAMMATORY MARKERS AS TOOLS IN THE DETECTION AND PREVENTION OF DIABETES MELLITUS AND AS TOOLS TO AID IN THE SELECTION OF AGENTS TO BE USED FOR THE PREVENTION AND TREATMENT OF DIABETES

(75) Inventors: Paul M. Ridker, Chestnut Hill, MA (US); JoAnn E. Manson, Beverly, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 55 days.

(21) Appl. No.: 10/017,905

(22) Filed: Dec. 14, 2001

(65) Prior Publication Data

US 2003/0100486 A1 May 29, 2003

Related U.S. Application Data

(60) Provisional application No. 60/255,632, filed on Dec. 14, 2000.

(51) Int. Cl.
*G01N 33/53* (2006.01)
(52) U.S. Cl. ..................................................... 435/7.1
(58) Field of Classification Search ................ 435/4, 7.1
See application file for complete search history.

(56) References Cited

U.S. PATENT DOCUMENTS 6,040,147 A * 3/2000 Ridker et al. ................ 435/7.24

OTHER PUBLICATIONS

Koenig et al., Circulation, 1999, vol. 99, pp. 237-242.*
Schalkwijk, C.G., et al. Diabetologia. Mar. 1999;42:351-357.*
Rodriguez-Moran, M., et al. J. Diabet. Comp. Jul.-Aug. 1999;13:211-215.*
Rohlfing, C.L., et al. Diabetes Care. 2000;23(2):187-191.*
Chapin, B.L., et al. Diabetes Care. 1999;22(3):436-429.*
Ford, E.S. Diabetes Care. 1999;22(12):1971-1977.*
Dods and Bolmey. Clin. Chem. 1979;25(5):764-768.*
www.emergencymedical.com/Definitions/Signs%20and%20Symptoms.htm, 2008.*
www.biology-online.org/dictionary/Signs_and_Symptoms, 2005.*
Connolly, K.M., et al. Annals Rheumatic Dis. 1988;47:515-521.*
El-Nawawy, A. et al., "Interleukin-1-β, Tumor Necrosis Factor-α, Insulin Secretion and Oral Glucose Tolerance in Non-Diabetic Siblings of Children with IDDM," *Indian J. Pediatr.* 1998; 65: 455-460.
Kallmann, B.A., et al. "Cytokine secretion patterns in twins discordant for Type I diabetes," *Diabetologia* 1999; 42: 1080-1085.
Kretowski, A. et al., "The immune markers of preclinical phase of type 1 diabetes meilitus. The role of cytokines, adhesion molecules and peripheral blood lymphocyte subpopulations in the pathogenesis and prediction of insulin-dependent diabetes," *Przeglad Lekurski* 2000; 57: (12) 736-742.
Kretowski, A. et al., "In Vitro Secretion of Interleukin 2 and Expression of IL-2 Receptor in Peripheral Blood Lymphocytes in High Risk of Insulin-Dependent Diabetes Mellitus Subjects," *Archivum Immunologiae et Therapiae Experimentalis* 1999; 47: 45-49.
Kretowski, A. et al., "Nicotinamide inhibits enhanced in vitro production of interleukin-12 and tumour necrosis factor-α in peripheral whole blood of people at high risk of developing Type 1 diabetes and people with newly diagnosed Type 1 diabetes," *Diabetes Research and Clinical Practice* 2000; 47: 81-86.
Szelachowska, M. et al., "Increased In Vitro Interleukin-12 Production by Peripheral Blood in High-Risk IDDM First Degree Relatives," *Horm Metab. Res.* 1997; 29: 168-171.
Asakura, Toshio "Glycosylated Hemoglobin (HbAlc) and Diabetes Mellitus", *Seitai no Kagaku*, May 1981, vol. 32, No. 3, p. 242-249 Abstract only.
Kumon, Y. et al. "Serum Amyloid A Protein in Patients with Non-Insulin-Dependent Diabetes Mellitus", *Clin. Biochem.*, Dec. 1994, vol. 27, No. 6, p. 469-473.
Nakahara, Rieko et al. "The Significance of Blood Leptin Concentration Measurements in Type 2 Diabetes patients", *Proceedings of the 47th National Congress of the Japanese Society of Laboratory Medicine*, Sep. 25, 2000, vol. 48, Supplement, p. 241. Abstract only.
Pickup et al., "Plasma interleukin-6, tumour necrosis factor alpha and blood cytokine production in type 2 diabetes," *Life Sciences*, Jun. 2000, vol. 67, pp. 291-300.
Uchimura, I. et al. "Interleukin-6 and its Hemorhelogical Effects in Diabetes Mellitus", *Biorheology*, 1992, vol. 29, No. 1, p. 27.
Vijan, N. et al., "Screening, Prevention, Counseling, and Treatment for the Complications of Type II Diabetes Mellitus. Putting Evidence into Practice" *J Gen Intern Med*, 1997, vol. 12, pp. 567-580.
Gail, M. et al., "Likelihood calculations for matched case-control studies and survival studies with tied death times," *Biometrika* 1981, 3(68), 703-707.
Shadick, N. et al., "C-Reactive Protein in the Prediction of Rheumatoid Arthritis in Women," *Arch Intern Med* 2006, 166, 2490-2494.
Carel et al., Treatment of prediabetic patients with insulin: experience and future. European Prediabetes Study Group. Horm Res. 1996;45 Suppl 1:44-7.
Keller et al., Insulin prophylaxis in individuals at high risk of type I diabetes. Lancet. Apr. 10, 1993;341(8850):927-8.
Khera et al., Race and gender differences in C-reactive protein levels. J Am Coll Cardiol. Aug. 2, 2005;46(3):464-9.

* cited by examiner

*Primary Examiner* — Gerald R Ewoldt
(74) *Attorney, Agent, or Firm* — Wolf, Greenfield & Sacks, P.C.

(57) ABSTRACT

The invention involves methods for characterizing an individual's risk profile of developing future diabetes or complications of diabetes by obtaining a level of an inflammatory marker in the individual. Preferred inflammatory markers according to the present invention include C reactive protein and interleukin-6. The invention also involves methods for evaluating the likelihood that an individual will benefit from treatment with an agent for reducing the risk of future diabetes.

19 Claims, 2 Drawing Sheets

INFLAMMATORY MARKERS AS TOOLS IN THE DETECTION AND PREVENTION OF DIABETES MELLITUS AND AS TOOLS TO AID IN THE SELECTION OF AGENTS TO BE USED FOR THE PREVENTION AND TREATMENT OF DIABETES

RELATED APPLICATIONS

This application claims priority under 35 U.S.C. §119(e) from Provisional U.S. patent application Ser. No. 60/255,632 filed on Dec. 14, 2000, entitled INFLAMMATORY MARKERS AS TOOLS IN THE DETECTION AND PREVENTION OF DIABETES MELLITUS AND AS TOOLS TO AID IN THE SELECTION OF AGENTS TO BE USED FOR THE PREVENTION AND TREATMENT OF DIABETES. The contents of the provisional application are hereby expressly incorporated by reference.

GOVERNMENT SUPPORT

The work leading to the present invention was funded in part by contract/grant numbers HL58755, HL43851, HL07575, and HL63293, from the United States National Heart, Lung, and Blood Institute, and CA47988 from the United States National Cancer Institute. Accordingly, the United States Government may have certain rights to this invention.

FIELD OF THE INVENTION

This invention describes the new use of a diagnostic test to determine the risk of diabetes mellitus, particularly among individuals with no signs or symptoms of current disease. Further, this invention describes the new use of diagnostic test to assist physicians in determining which individuals at risk will preferentially benefit from certain treatments designed either to prevent or treat diabetes.

BACKGROUND OF THE INVENTION

Despite significant advances in therapy, diabetes remains a major cause of morbidity and mortality in the developed world and early detection of diabetes is an area of major public health importance. However, it has been estimated that as many as 50 percent of individuals with diabetes are undiagnosed. It is for this reason that up to 30 percent of patients with "newly diagnosed" type II diabetes already have evidence of systemic complications at the time of diagnosis, data which suggest that the disease has been present already for 5 to 10 years.

Current techniques for screening for diabetes include a fasting glucose in excess of 140 mg/dL or higher on two occasions, or symptoms of uncontrolled diabetes with a random blood glucose in excess of 200 mg/dL, or a positive oral glucose tolerance test. In addition, the use of glycosylated hemoglobin levels has recently been advocated such that individuals with levels above 7.0 percent are considered to have early evidence of disease and thus are potential candidates for diet, exercise, or pharmacologic intervention.

Unfortunately, none of these tests have been found to detect all incident cases of diabetes, and the poor reproducibility and clinical inconvenience of the oral glucose tolerance test has limited its application. Moreover, accumulating data suggests that the beneficial effects of certain preventive and therapeutic treatments for patients at risk for or known to have diabetes differs in magnitude among different patient groups. At this time, however, data describing diagnostic tests to determine whether certain therapies can be expected to be more or less effective in the prevention and treatment of diabetes are lacking.

C-reactive protein is a known marker for underlying systemic inflammation. Elevated levels of C-reactive protein have been described among patients with overt clinical evidence of diabetes and among individuals with evidence of glucose intolerance. However, it has been uncertain whether statistical associations observed in these prior studies of patients with overt disease are causal, are due to short-term inflammatory changes, or are due to interrelations with other risk factors such as obesity and hyperlipidemia.

A need exists for the development of tests that assess the risks for an individual developing future diabetes or diabetic complications.

SUMMARY OF THE INVENTION

This invention describes new diagnostic tests for assessing the risk for future development of diabetes or diabetic complications in an individual. These new tests broadly include (1) the prediction of risk of developing clinically apparent diabetes; and (2) the determination of the likelihood that certain individuals will benefit to a greater or lesser extent from the use of certain treatments designed to prevent and/or treat diabetes. These new tests are based in part upon the following discoveries. It has been discovered that elevated levels of certain markers of systemic inflammation are predictive of future development of diabetes or diabetic complications. For example, elevated levels of C-Reactive Protein and/or Interleukin-6 in apparently healthy, middle aged individuals are predictive of an increased risk of diabetes or diabetic complications. As another example, contrary to suggestions in the prior art, elevated levels of certain markers of systemic inflammation in otherwise healthy men and women are predictive of an increased risk of a diabetes or diabetic complications even after controlling for other factors such as obesity, hypertension, hyperlipidemia, and a family history of diabetes. As still another example, elevated levels of certain markers of systemic inflammation are predictive of an increased likelihood of developing diabetes or diabetic complications even among apparently healthy individuals with a glycosylated hemoglobin (HbA1c) level below 7.0 percent, 6.5 percent and even 6.0 percent, levels well below those currently-considered to be indicative of future risk of developing this diabetes or diabetic complications.

It has been discovered also that the likelihood that certain individuals will benefit to a greater or a lesser extent from the use of certain therapeutic agents for reducing the risk of a future diabetes or diabetic complications can be determined from the base-line level of certain markers of systemic inflammation in an individual.

It further has been discovered that the predictive value of certain markers of systemic inflammation are independent of other predictors and, for example, are least additive with risk factors such as glycosylated hemoglobin screening. Thus, the level of markers of systemic inflammation does not simply duplicate that which is measured when levels of a second risk factor (e.g., glycosylated hemoglobin) are obtained. Therefore, the combination of these two methods of early detection is substantially better than that associated with current methods.

As mentioned above, these discoveries have led to new diagnostic tests.

Thus, according to one aspect of the invention, a method for evaluating the likelihood that an individual will benefit from treatment with an agent for reducing the risk of diabetes or reducing the risk of diabetic complications is provided. The agent can be selected from the group consisting of insulin, a hypoglycemic agent, an anti-inflammatory agent, a lipid lowering agent, a calcium channel blocker, a beta-adrenergic receptor blocker, a cyclooxygenase-2 inhibitor, and an angiotensin system inhibitor. To practice the method, a level of a certain marker of systemic inflammation in an individual is obtained. This level then is compared to a predetermined value specific for the diagnosis of diabetes or diabetic complications, wherein the level of the marker of systemic inflammation in comparison to the predetermined value is indicative of whether the individual will benefit from treatment with the agent. The individual then can be characterized in terms of the net benefit likely to be obtained by treatment with the agent.

The predetermined value specific for the diagnosis of diabetes or diabetic complications can be a single value, multiple values, a single range or multiple ranges. Thus, in one embodiment, the predetermined value is a plurality of predetermined marker level ranges, and the comparing step comprises determining in which of the predetermined marker level ranges the individual's level falls. In preferred embodiments, the individual is apparently healthy. In certain embodiments, the individual also is a nonsmoker. In preferred embodiments the marker of systemic inflammation is selected from the group consisting of C-reactive protein (CRP), and a cytokine. In the most preferred embodiment, the marker of systemic inflammation is C-reactive protein. In a further important embodiment, the marker of systemic inflammation is interleukin-6 (IL-6, a cytokine). Particularly useful results have been obtained with the foregoing markers of systemic inflammation. In certain embodiments, the invention does not embrace the inflammatory markers selected from the group consisting of white cell count, albumin, fibrinogen, serum sialic acid, orosomucoid, haptoglobin, and $\alpha_1$-antitrypsin.

When the marker of systemic inflammation is C-reactive protein, then a preferred predetermined value is about 0.30 mg/dL of blood. Another preferred predetermined value is about 0.60 mg/dL of blood. When ranges are employed, it is preferred that one of the plurality of ranges be below about 0.30 mg/dL of blood and that another of the ranges be above about 0.30 mg/dL of blood. When the marker of systemic inflammation is interleukin-6, then a preferred predetermined value is about 1.39 pg/mL of blood or higher. Another preferred predetermined value when the marker of systemic inflammation is interleukin-6, is about 2.05 pg/mL of blood. The predetermined value will depend, of course, on the particular marker selected and even upon the characteristics of the patient population in which the individual lies, described in greater detail below.

As mentioned above, the invention is particularly adapted to determining which individuals will preferentially benefit from treatment with an agent for reducing the risk in the individuals of developing diabetes or diabetic complications. It also permits selection of candidate populations for clinical trials and for treatment with candidate drugs, by identifying, for example, the individuals most likely to benefit from a new treatment or from a known treatment with a high risk profile of adverse side effects. Thus, the invention provides information for evaluating the likely net benefit of certain treatments for candidate patients.

According to another aspect of the invention, a method is provided for characterizing an individual's risk profile of developing future diabetes or diabetic complications. The method involves obtaining a level of a marker of systemic inflammation in the individual. The level of the marker then is compared to a predetermined value specific for the diagnosis of diabetes or diabetic complications, and the individual's risk profile of developing a future diabetes or diabetic complications is then characterized based upon the level of the marker in comparison to the predetermined value. As in the previous aspect of the invention, the predetermined value specific for the diagnosis of diabetes or diabetic complications may be a single value, a plurality of values, a single range or a plurality of ranges. In one embodiment, the predetermined value is a plurality of predetermined marker level ranges and the comparing step involves determining in which of the predetermined marker level ranges the individual's level falls. The individual characterized may be any individual, but preferably is an apparently healthy individual. The apparently healthy individual can be a smoker or a nonsmoker.

According to yet another aspect of the invention, a method is provided in which one uses an inflammatory marker together with a "known diabetic marker/test" for characterizing an individual's risk profile of developing future diabetes and diabetic complications. A "known diabetic marker/test," as used herein, refers to known markers and methods used by one of ordinary skill in the art to detect diabetes, and include glycosylated hemoglobin and/or oral glucose tolerance testing. In an important embodiment, a level of a marker of systemic inflammation in the individual is obtained. The level of the marker is compared to a predetermined value specific for the diagnosis of diabetes or diabetic complications to establish a first risk value. A level of a known diabetic marker/test, such as that of glycosylated hemoglobin, in the individual also is obtained. The level of the glycosylated hemoglobin in the individual is compared to a second predetermined value specific for the diagnosis of diabetes or diabetic complications to establish a second risk value. The individual's risk profile of developing diabetes or diabetic complications then is characterized based upon the combination of the first risk value and the second risk value, wherein the combination of the first risk value and second risk value establishes a third risk value different from the first and second risk values. In particularly important embodiments, the third risk value is greater than either of the first and second risk values. The preferred individuals for testing, markers and predetermined values are as described above.

The invention also contemplates kits comprising a package including an assay for a marker of systemic inflammation and instructions, and optionally related materials such as number or color charts, for correlating the level of the marker as determined by the assay with a risk of developing future diabetes or diabetic complications or with other patient criteria as described above. In important embodiments, the kits also include an assay for a glycosylated hemoglobin.

According to still another aspect, a method for treating subjects to reduce the risk of diabetes or a diabetic complication in the subjects is provided. The method involves selecting and administering to a subject in need of such treatment an agent for reducing the risk of diabetes in an amount effective to lower the risk of the subject developing diabetes or a diabetic complication, wherein the agent is selected from the group consisting of insulin, a hypoglycemic agent, an anti-inflammatory agent, a lipid lowering agent, a calcium channel blocker, a beta-adrenergic receptor blocker, a cyclooxygenase-2 inhibitor, and an angiotensin system inhibitor. The preferred subjects are apparently healthy subjects free of current need for treatment with any of the foregoing agents.

In important therapeutic embodiments, an anti-inflammatory agent is the agent preferably administered to a subject to reduce the risk of diabetes or a diabetic complication developing in the subject. In certain embodiments, the inflammatory agent is a cytokine inhibitor. In some embodiments, the inflammatory agent is a Tumor Necrosis Factor-α (TNF-α) inhibitor. Preferred TNF-α inhibitors include Etanercept and Infliximab.

The invention is thus useful in providing an earlier method of detection of diabetes or a diabetic complication, also leading to increased surveillance and/or increased frequency of use of currently available methods for diabetes screening.

These and other aspects of the invention will be described in more detail below in connection with the detailed description of the invention.

DETAILED DESCRIPTION OF THE INVENTION

Figure 1:
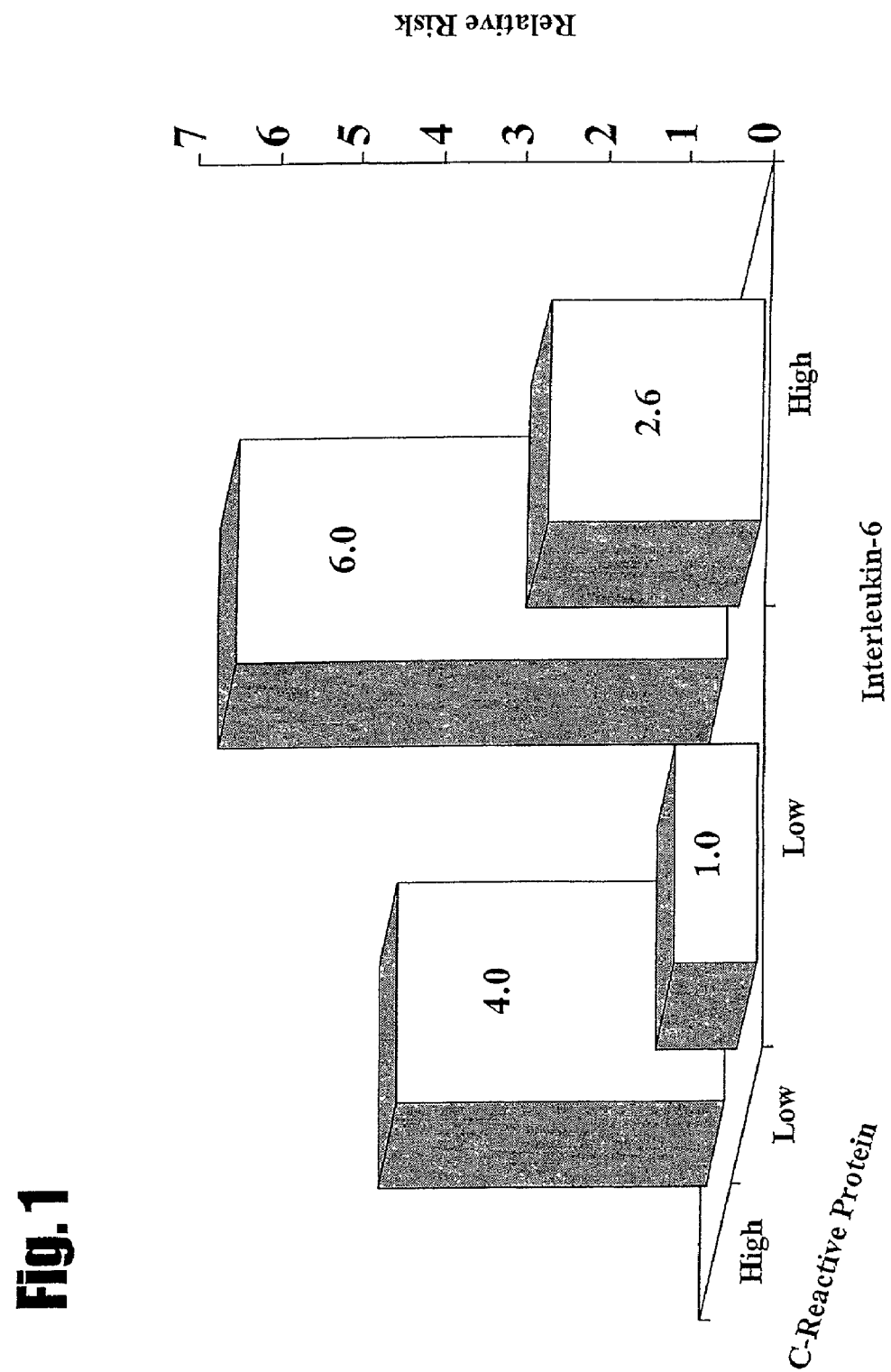
FIG. 1 is a bar graph showing relative risk of incident diabetes mellitus in subjects according to baseline level of IL-6 and CRP; groups were formed based on the 75th percentile cut-point value of each IL-6 and/or CRP using distributions of control subjects in the study population.

The primary basis for this invention is evidence from the Women's Health Study, a large scale, randomized, double-blind, placebo-controlled primary prevention of cardiovascular disease trial of aspirin and vitamin E conducted among 28,000 apparently healthy women. In that trial, baseline level of C reactive protein, a marker for underlying systemic inflammation, was found to determine the future risk of developing diabetes or diabetic complications independent of a large series of other risk factors. Specifically, individuals with the highest baseline levels of C-reactive protein were found to have more than a 10 fold increase in risk of developing future diabetes, even when the baseline glycosylated hemoglobin level was below 6.0; among such individuals, the crude relative risks of developing future diabetes for those with baseline levels of C-reactive protein from the lowest to highest quartiles were 1.0, 2.2, 8.7, and 15.7 (P-trend<0.001). In this analysis, the quartile cut-points for C-reactive protein were: ≦0.10, 0.11-0.26, 0.27-0.61, and >0.61 mg/dL, respectively.

Moreover, this effect remained statistically significant after adjusting for body mass index, hypertension, family history of diabetes, exercise frequency, alcohol consumption, hyperlipidemia, smoking, and menopausal status. In this fully adjusted analysis, again limited to those apparently healthy women with glycosylated hemoglobin levels below 6.0 percent, the relative risks of developing future diabetes for those with baseline levels of C reactive protein from the lowest to highest quartiles were 1.0, 1.3, 4.1, and 4.2 (P-trend 0.001). (See, e.g., Table 3).

Further, data from the foregoing Women's Health Study show that the risks of future diabetes appear to be additive to that which could otherwise be determined by usual assessment of a known diabetes test/marker, such as, for example, glycosylated hemoglobin. These data also raised the possibility that agents that enhance C reactive protein production may have an important role in determining the risk of diabetes. This hypotheses was tested; data deriving from this study with regard to interleukin-6 (IL-6), a cytokine largely responsible for C reactive protein production in the liver, confirmed that this inflammatory marker can also predict diabetic risk. Among individuals in the Women's Health Study, the crude relative risks of developing future diabetes for those with baseline levels of IL-6 from the lowest to highest quartiles were 1.0, 2.5, 4.1, and 7.5 (P-trend<0.001). In this analysis, the quartile cut-points for IL-6 were: ≦0.91, 0.92-1.38, 1.39-2.05, and >2.05 pg/mL, respectively. (See, e.g., Table 2).

Moreover, this effect remained statistically significant after adjusting for body mass index, hypertension, family history of diabetes, exercise frequency, alcohol consumption, hyperlipidemia, smoking, and menopausal status. In this fully adjusted analysis, again limited to those apparently healthy women with glycosylated hemoglobin levels below 6.0 percent, the relative risks of developing future diabetes for those with baseline levels of IL-6 from the lowest to highest quartiles were 1.0, 1.4, 1.3, and 2.3 (P-trend<0.001). (See, e.g., Table 2).

The current invention in one aspect describes the use of C reactive protein, an inflammatory marker, to predict risk of diabetes among apparently healthy individuals with no prior evidence of disease. Thus, these data greatly extend prior observations which have suggested that C reactive protein levels are increased among individuals who already are known to have this disorder. Indeed, it has been uncertain whether statistical associations observed in prior studies of individuals with known diabetes are casual or due to short-term inflammatory changes, or to interrelations with other risk factors, in particular obesity and hyperlipidemia.

In marked contrast, data from the Women's Health Study indicate for the first time the utility of C reactive protein and other inflammatory markers to predict risk of future diabetes among currently healthy and otherwise low-risk individuals, and to predict risk above and beyond that associated with screening for other known diabetic markers/tests such as glycosylated hemoglobin and oral glucose tolerance. Data from the Women's Health Study also suggest for the first time that C reactive protein levels in healthy individuals might be used to increase the frequency of surveillance with other screening techniques for diabetes (see earlier discussion on other known diabetic markers/tests), and that the efficacy and timing of interventions designed to prevent the onset of diabetes or reduce the severity of diabetic complications may differ in magnitude based upon a measure of the extent of underlying systemic inflammation.

The invention will be better understood with reference to the following brief explanation of terms.

"Diabetes," as used herein, refers to diabetes mellitus (both Type I: insulin-dependent diabetes mellitus, and type II: non-insulin-dependent diabetes mellitus), and includes insulin resistance syndrome such as prereceptor resistance (mutated insulins, anti-insulin antibodies), and receptor and postreceptor resistance (obesity, absent or dysfunctional receptor, antibody to insulin receptor, lipodystrophic states, leprechaunism, ataxia-telangiectasia, Rabson-Mendenhall syndrome, Werner syndrome, Alström syndrome, pineal hyperplasia syndrome).

"Diabetic complications," as used herein, refer to acute metabolic complications (diabetic ketoacidosis, hyperosmolar coma), and late complications (circulatory abnormalities, retinopathy, diabetic nephropathy, diabetic neuropathy, diabetic foot ulcers).

A more detailed description of the foregoing terms can be obtained from a number of sources known in the art (see, e.g., Harrison's Principles of Experimental Medicine, 13th Edition, McGraw-Hill, Inc., N.Y)

"Apparently healthy", as used herein, means individuals who have not previously had any clinical evidence of diabetes and who do not otherwise exhibit symptoms of disease. In other words, such individuals, if examined by a medical professional, would be characterized as healthy and free of symptoms of disease.

"Nonsmoking", as used herein, means an individual who, at the time of the evaluation, is not a smoker. This includes individuals who have never smoked as well as individuals who in the past have smoked but presently no longer smoke.

Agents for reducing the risk of diabetes or diabetic complications include those selected from the group consisting of insulin, hypoglycemic agents, anti-inflammatory agents, lipid lowering agents, calcium channel blockers, beta-adrenergic receptor blockers, cyclooxygenase-2 inhibitors, and angiotensin system inhibitors.

"Insulin" includes rapid acting forms, such as Insulin lispro rDNA origin: HUMALOG® (1.5 mL, 10 mL, Eli Lilly and Company, Indianapolis, Ind.), Insulin Injection (Regular Insulin) form beef and pork (regular ILETIN® I, Eli Lilly], human: rDNA: HUMULIN® R (Eli Lilly), NOVOLIN® R (Novo Nordisk, New York, N.Y.), Semisynthetic: VELOSULIN® Human (Novo Nordisk), rDNA Human, Buffered: VELOSULIN® BR, pork: regular Insulin (Novo Nordisk), purified pork: Pork Regular ILETIN® II (Eli Lilly), Regular Purified Pork Insulin (Novo Nordisk), and Regular (Concentrated) ILETIN® II U-500 (500 units/mL, Eli Lilly); intermediate-acting forms such as Insulin Zinc Suspension, beef and pork: LENTE® ILETIN® I (Eli Lilly), Human, rDNA: HUMULIN® L (Eli Lilly), NOVOLIN® L (Novo Nordisk), purified pork: LENTE® ILETIN® II (Eli Lilly), Isophane Insulin Suspension (NPH): beef and pork: NPH ILETIN® I (Eli Lilly), Human, rDNA: HUMULIN® N (Eli Lilly), Novolin® N (Novo Nordisk), purified pork: Pork NPH Iletin® II (Eli Lilly), NPH-N (Novo Nordisk); and long-acting forms such as Insulin zinc suspension, extended (ULTRALENTE®, Eli Lilly), human, rDNA: HUMULIN® U (Eli Lilly).

"Hypoglycemic" agents are preferably oral hypoglycemic agents and include first-generation sulfonylureas: Acetohexamide (Dymelor), Chlorpropamide (Diabinese), Tolbutamide (Orinase); second-generation sulfonylureas: Glipizide (Glucotrol, Glucotrol XL), Glyburide (Diabeta; Micronase; Glynase), Glimepiride (Amaryl); Biguanides: Metformin (Glucophage); Alpha-glucosidase inhibitors: Acarbose (Precose), Miglitol (Glyset), Thiazolidinediones: Rosiglitazone (Avandia), Pioglitazone (Actos), Troglitazone (Rezulin); Meglitinides: Repaglinide (Prandin); and other hypoglycemics such as Acarbose; Buformin; Butoxamine Hydrochloride; Camiglibose; Ciglitazone; Englitazone Sodium; Darglitazone Sodium; Etoformin Hydrochloride; Gliamilide; Glibomuride; Glicetanile Gliclazide Sodium; Gliflumide; Glucagon; Glyhexamide; Glymidine Sodium; Glyoctamide; Glyparamide; Linogliride; Linogliride Fumarate; Methyl Palmoxirate; Palmoxirate Sodium; Pirogliride Tartrate; Proinsulin Human; Seglitide Acetate; Tolazamide; Tolpyrramide; Zopolrestat. Further hypoglycemic agents are described in detail in U.S. Pat. Nos.: 6,121,282, 6,057,343, 6,048,842, 6,037,359, 6,030,990, 5,990,139, 5,981,510, 5,980,902, 5,955,481, 5,929,055, 5,925,656, 5,925,647, 5,916,555, 5,900,240, 5,885,980, 5,849,989, 5,837,255, 5,830,873, 5,830,434, 5,817,634, 5,783,556, 5,756,513, 5,753,790, 5,747,527, 5,731,292, 5,728,720, 5,708,012, 5,691,386, 5,681,958, 5,677,342, 5,674,900, 5,545,672, 5,532,256, 5,531,991, 5,510,360, 5,480,896, 5,468,762, 5,444,086, 5,424,406, 5,420,146, RE34,878, 5,294,708, 5,268,373, 5,258,382, 5,019,580, 4,968,707, 4,845,231, 4,845,094, 4,816,484, 4,812,471, 4,740,521, 4,716,163, 4,695,634, 4,681,898, 4,622,406, 4,499,279, 4,467,681, 4,448,971, 4,430,337, 4,421,752, 4,419,353, 4,405,625, 4,374,148, 4,336,391, 4,336,379, 4,305,955, 4,262,018, 4,220,650, 4,207,330, 4,195,094, 4,172,835, 4,164,573, 4,163,745, 4,141,898, 4,129,567, 4,093,616, 4,073,910, 4,052,507, 4,044,015, 4,042,583, 4,008,245, 3,992,388, 3,987,172, 3,961,065, 3,954,784, 3,950,518, 3,933,830, the disclosures of which patents are incorporated herein by reference.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. An important anti-inflammatory agent is aspirin.

Preferred anti-inflammatory agents are cytokine inhibitors. Important cytokine inhibitors include cytokine antagonists (e.g., IL-6 receptor antagonists), aza-alkyl lysophospholipids (AALP), and Tumor Necrosis Factor-α (TNF-α) inhibitors, such as anti-TNF-α antibodies, soluble TNF receptor, TNF-α anti-sense nucleic acid molecules, multivalent guanylhydrazone (CNI-1493), N-acetylcysteine, pentoxiphylline, oxentifylline, carbocyclic nucleoside analogues, small molecule S9a, RP 55778 (a TNF-α synthesis inhibitor), Dexanabinol (HU-211, is a synthetic cannabinoid devoid of cannabimimetic effects, inhibits TNF-α production at a post-transcriptional stage), MDL 201,449A (9-[(1R, 3R)-trans-cyclopentan-3-ol] adenine, and trichodimerol (BMS-182123). Preferred TNF-α inhibitors are Etanercept (ENBREL®, Immunex, Seattle) and Infliximab (REMICADE®, Centocor, Malvern, Pa.). Further TNF-α inhibitors are described in detail in U.S. Pat. Nos.: 6,143,866, 6,127,378, 6,103,702, 5,998,378, 5,985,592, 5,972,928, 5,877,180, 5,853,977, 5,849,501, 5,846,755, 5,843,675, 5,830,742, 5,820,858, 5,795,574, 5,762,921, 5,747,532, 5,691,382, 5,660,826, 5,654,312, and 5,091,511.

"Lipid reducing agents" include gemfibrozil, cholystyramine, colestipol, nicotinic acid, and HMG-CoA reductase inhibitors. HMG-CoA (3-hydroxy-3-methylglutaryl-coenzyme A) reductase is the microsomal enzyme that catalyzes the rate limiting reaction in cholesterol biosynthesis (HMG-CoA Mevalonate). An HMG-CoA reductase inhibitor inhibits HMG-CoA reductase, and as a result inhibits the synthesis of cholesterol. A number of HMG-CoA reductase inhibitors has been used to treat individuals with hypercholesterolemia. More recently, HMG-CoA reductase inhibitors have been shown to be beneficial in the treatment of stroke (Endres M, et al., *Proc Natl Acad Sci U S A*, 1998, 95:8880-5).

HMG-CoA reductase inhibitors useful for administration, or co-administration with other agents according to the invention include, but are not limited to, simvastatin (U.S. Pat. No. 4, 444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622, 985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402, the disclosures of which patents are incorporated herein by reference.

"Calcium channel blockers" are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p. 13-16 (1983); Fleckenstein, *Experimental Facts and Therapeutic Prospects*, John Wiley, New York (1983); McCall, D., *Curr Pract Cardiol*, v. 10, p. 1-11 (1985)). Calcium channel blockers are a heterogeneous group of drugs that prevent or slow the entry of calcium into cells by regulating cellular calcium channels. (Remington, *The Science and Practice of Pharmacy*, Nineteenth Edition, Mack Publishing Company, Eaton, Pa., p.963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

Cyclooxygenase-2 (COX-2) is a recently identified form of a cyclooxygenase. "Cyclooxygenase" is an enzyme complex present in most tissues that produces various prostaglandins and thromboxanes from arachidonic acid. Non-steroidal, anti-inflammatory drugs exert most of their anti-inflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the COX-1. COX-2 is rapidly and readily inducible by a number of agents including mitogens, endotoxin, hormones, cytokines and growth factors. As prostaglandins have both physiological and pathological roles, the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar anti-inflammatory, antipyretic and analgesic properties to a conventional non-steroidal anti-inflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S.

Pat. No. 5,604,260 "5-methanesulfonamido-1-indanones as an inhibitor of cyclooxygenase-2"; U.S. Pat. No. 5,639,780 "N-benzyl indol-3-yl butanoic acid derivatives as cyclooxygenase inhibitors"; U.S. Pat. No. 5,677,318 "Diphenyl-1,2,3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenyl-heterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An "angiotensin system inhibitor" is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [($San^1$)($Val^5$)($Ala^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J. Pharmacol. Exp. Ther.* 247(1), 1-7 (1988)); 4,5,6,7-tetrahydro-1H-imidazo [4,5-c] pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35,45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G. D. Searle and Company).

"Angiotensin converting enzyme (ACE), is an enzyme which catalyzes the conversion of angiotensin I to angiotensin II. ACE inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410, 520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

In practicing the methods of the present invention, it is required to obtain a level of a marker of systemic inflammation in an individual. Markers of systemic inflammation are well-known to those of ordinary skill in the art. It is preferred that the markers of systemic inflammation be selected from the group consisting of C-reactive protein, and cytokines. Cytokines are well-known to those of ordinary skill in the art and include human interleukins 1-17. The level of C reactive protein can be obtained by any art recognized method although for this application, a highly sensitive assay is required. Typically, the level is determined by measuring C reactive protein in a body fluid, for example, blood, lymph, saliva, urine and the like. The level can be determined by ELISA, or immunoassays or other conventional techniques for determining the presence of C reactive protein. Conventional methods include sending samples of a patient's body fluid to a commercial laboratory for measurement.

The invention also involves comparing the level of C reactive protein with a predetermined value specific for the diagnosis of diabetes or diabetic complications. The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quadrants, the lowest quadrant being individuals with the lowest risk and the highest quadrant being individuals with the highest risk.

The predetermined value specific for the diagnosis of diabetes or diabetic complications can depend upon the particular population selected. For example, an apparently healthy, nonsmoker population (no detectable disease and no prior history of diabetes) will have a different 'normal' range of, for example, C reactive protein than will a smoking population or a population selected on the basis of obesity. Accordingly, the predetermined values selected may take into account the category in which an individual falls. Appropriate ranges and categories can be selected with no more than routine experimentation by those of ordinary skill in the art.

The preferred body fluid is blood and the preferred marker is C-reactive protein. For C-reactive protein, one important cut-off for a population of apparently healthy individuals is 0.30 mg/dL (median). Another important cut-off for C-reactive protein is 0.60 mg/dL (highest quartile of risk). In characterizing risk, numerous predetermined values can be established. In a preferred embodiment, the cut-off values described above are surprisingly lower than those shown in the prior art where C-reactive protein levels are studied in individuals who already are known to have severe diabetes or are already suffering from systemic complications of the disease. "A predetermined value specific for the diagnosis of diabetes or diabetic complications," as used herein, refers to a value that was not known previously to be associated with diabetes or diabetic complications, and expressly excludes, in the case of C reactive protein as the inflammatory marker, values less than about 0.20 mg/dL, and even less than about 0.25 mg/dL.

There presently are commercial sources which produce reagents for assays for C-reactive protein. These include, but are not limited to, Dade-Behring (Newark, Del.), Abbott Pharmaceuticals (Abbott Park, Ill.), CalBiochem (San Diego, Calif.), Kamiya Diagnsotics (Japan), and Behringwerke (Marburg, Germany).

In preferred embodiments the invention provides novel kits or assays which are specific for, and have appropriate sensitivity with respect to, predetermined values selected on the basis of the present invention. The preferred kits, therefore, would differ from those presently commercially available, by including, for example, different cut-offs, different sensitivities at particular cut-offs as well as instructions or other printed material for characterizing risk based upon the outcome of the assay.

As discussed above, the invention provides methods for evaluating the likelihood that an individual will benefit from early treatment with an agent for reducing risk of a future diabetes or reducing the risk of diabetic complications. This method has important implications for patient treatment and also for clinical development of new therapeutics. Physicians select therapeutic regimens for patient treatment based upon the expected net benefit to the patient. The net benefit is derived from the risk to benefit ratio. The present invention permits selection of individuals who are more likely to benefit by intervention, thereby aiding the physician in selecting a therapeutic regimen. This might include using drugs with a higher risk profile where the likelihood of expected benefit has increased. Likewise, clinical investigators desire to select for clinical trials a population with a high likelihood of obtaining a net benefit. The present invention can help clinical investigators select such individuals. It is expected that clinical investigators now will use the present invention for determining entry criteria for clinical trials.

In another surprising aspect of the invention, it has been discovered that C reactive protein and/or IL-6 have predictive values independent of other known predictors of future risk of diabetes. Thus, the present invention does not involve simply duplicating a measurement that previously could be made using other predictors. Instead, the use of C reactive protein and/or IL-6 to determine diabetic risk is additive to prior art predictors, including glycosylated hemoglobin. Moreover, even among apparently healthy individuals with low levels of glycosylated hemoglobin (less than 6.5 percent or less than 6.0 percent), elevated levels of C reactive protein and/or IL-6 have been found to predict onset of diabetes. Thus, use of C reactive protein and/or IL-6 screening, for example among individuals with a family history of diabetes might be used to increase the frequency of surveillance with standard tests for diabetes such as glycosylated hemoglobin of oral glucose tolerance testing. As is also abundantly clear from data discovered in the Women's Health Study (see Examples), the risk of future diabetes is at least additive to that associated with the risk of elevated levels of glycosylated hemoglobin.

The invention also involves a method for treating subjects to reduce the risk of diabetes or a diabetic complication in the subjects. The method involves selecting (according to any of the methods of the invention based upon the level of an inflammatory marker) and administering to a subject in need of such treatment an agent for reducing the risk of diabetes in an amount effective to lower the risk of the subject developing diabetes or a diabetic complication. The agent is selected from the group consisting of insulin, a hypoglycemic agent, an anti-inflammatory agent, a lipid lowering agent, a calcium channel blocker, a beta-adrenergic receptor blocker, a cyclooxygenase-2 inhibitor, and an angiotensin system inhibitor. Preferably, the subject is free of symptoms calling for treatment with any of the foregoing agents. The agent is administered in an effective amount.

An effective amount is a dosage of the anti-inflammatory agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health practitioner. For example, an effective amount can depend upon the degree to which an individual has abnormally elevated levels of markers of systemic information. It should be understood that the agents of the invention are used to prevent diabetes or diabetic complications, that is, they are used prophylactically in subjects at risk of developing diabetes or diabetic complications. Thus, an effective amount is that amount which can lower the risk of, slow or perhaps prevent altogether the development of diabetes or diabetic complications. It will be recognized when the agent is used in acute circumstances, it is used to prevent one or more medically undesirable results that typically flow from such adverse events. In the case of diabetes, the agent (e.g., hypoglycemic agent) can be used to limit ketoacidocis. Generally, doses of active compounds would be from about 0.01 mg/kg per day to 1000 mg/kg per day. It is expected that doses ranging from 50-500 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The agents of the invention may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the agent of choice, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the agent into association with a carrier which constitutes one or more accessory ingredients. In general, the compositions are prepared by uniformly and intimately bringing the anti-inflammatory agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of an agent of the present invention, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active ingredient for at least 30 days, and preferably 60 days. Long-term sustained release implants are well-known to those of ordinary skill in the art and include some of the release systems described above. Specific examples include, but are not limited to, long-term sustained release implants described in U.S. Pat. No. 4,748,024, and Canadian Patent No. 1330939.

An agent of the invention can be administered by itself, or co-administered in combination with other agents of the invention. "Co-administering," as used herein, refers to administering simultaneously two or more compounds of the invention (e.g., insulin and a hypoglycemic agent), as an admixture in a single composition, or sequentially, close enough in time so that the compounds may exert an additive or even synergistic effect, i.e., on reducing the risk of developing diabetes or diabetic complications.

The invention will be more fully understood by reference to the following examples. These examples, however, are merely intended to illustrate the embodiments of the invention and are not to be construed to limit the scope of the invention.

EXAMPLES

Example 1

Methods
Study Participants

We designed a prospective, nested case-control study involving participants in the Women's Health Study (WHS), an ongoing trial evaluating the balance of benefits and risks of low-dose aspirin and vitamin E in the primary prevention of cardiovascular disease and cancer among female health professionals aged 45 years and older.[16] Seventy-one percent of WHS participants provided whole blood samples at enrollment. These were centrifuged and stored in liquid nitrogen until laboratory analysis. EDTA plasma samples were used for IL-6, CRP, and insulin determination. Packed red blood cell samples were used for measurement of hemoglobin A1c.

Case subjects were WHS participants providing blood specimens who were free of reported diabetes at enrollment and subsequently developed newly diagnosed diabetes during a four-year observation period. Candidate cases were initially identified by self-report on yearly follow-up questionnaires and subsequently verified through telephone interview conducted by a physician (ADP). Based on revised ADA diagnostic criteria,[17] cases were confirmed if one or more of the following conditions were met: (1) presence of >1 classic symptom of hyperglycemia (polyuria, polydipsia, weight loss with or without polyphagia, and blurred vision) plus either a fasting glucose>126 mg/dl ([7.0 mmol/l]) or random plasma glucose>200 mg/dl ([11.1 mmol/l]), or (2) in the absence of symptoms, >2 elevated plasma glucose concentrations (fasting>126 mg/dl ([7.0 mmol/l]), random>200 mg/dl ([11.1 mmol/l]), or 2-hour plasma glucose>200 mg/dl ([11.1 mmol/l]) during oral glucose tolerance testing), or (3) use of insulin or oral hypoglycemic agent. The primary care physician's office was contacted for supporting documentation as necessary. Candidate cases who either did not meet diagnostic criteria, were found to have prevalent diabetes at enrollment, or who died or were otherwise lost to follow-up were eliminated from consideration. In addition, to reduce misclassification bias due to undiagnosed diabetes at study entry, individuals diagnosed within the first year of follow-up (n=69) were excluded.

For each woman who developed confirmed incident diabetes, two control subjects were chosen at random among individuals free of self-reported diabetes mellitus at the time the case reported her event. Controls were matched by age (within one year) and fasting status of submitted blood specimen. Fasting was defined as >10 hours since last meal prior to sample collection. The study group undergoing laboratory investigation comprised 288 confirmed cases and 576 matched controls.

Due to the high prevalence of undiagnosed diabetes among middle-aged Americans and because this study was designed to evaluate the role of inflammation as a determinant of future diabetes, we further limited our sample to individuals with baseline hemoglobin A1c<6.5%, a reference value commonly used in clinical practice. Participants with missing values for baseline clinical covariates of interest were also eliminated from the analysis (body-mass index, 3% of cases and 1.5% of controls; history of hypertension 0.5% of cases and 0.7% of controls; history of hyperlipidemia, 0.5% of controls; and use of hormone replacement therapy, 0.3% of controls). The primary sample thus comprised 188 cases and 362 age-matched controls with HbA1c<6.5% on entry into the cohort. Among the subgroup of women providing fasting specimens we also measured specific insulin as an indicator of underlying insulin resistance.

Procedures

Baseline plasma samples were thawed and assayed for IL-6, CRP, and specific insulin (hereforth called 'insulin'). HbA1c was measured by immunoassay (Hitachi 911 Analyzer). Interleukin-6 was measured by a commercially available ELISA (R & D Systems, Minneapolis, Minn.). C-reactive protein was measured via a high-sensitivity latex-enhanced immunonephelometric assay on a BN II analyzer (Dade Behring, Newark, Del.).[18] Double antibody systems (Linco Research, St. Louis, Mo.) with less than 0.2% cross-reactivity between insulin and its precursors were used to measure specific concentrations of plasma insulin. In addition, as insulin levels may be falsely lowered in the presence of hemolysis,[19] specimens with free hemoglobin values>50 mg/dl (spectrophotometric method, Hitachi 911 Analyzer) were excluded from fasting subgroup investigations. Samples were analyzed in randomly ordered case-control triplets so as to reduce systematic bias and interassay variation.

Statistical Analysis

We used the Student's t-test to evaluate differences in means and the $\chi^2$ statistic for differences in proportions among case and control subjects comprising the primary study population. Because the distributions of IL-6, CRP, and insulin are skewed, differences in medians were tested with the Wilcoxon rank-sum test. Analysis of linear trends was used to assess associations between increasing level of each biomarker and risk of future diabetes after the sample was divided into quartiles based upon the distribution of controls. Quartile-specific risk estimates were obtained through conditional logistic regression adjusting for body-mass index (BMI, defined as $kg/m^2$), family history of diabetes in a first-degree relative, smoking, physical activity, alcohol consumption, and use of hormone replacement therapy. Continuous and categorical variables were specified according to best fit through comparison of competing conditional logistic regression models. In particular, BMI was controlled for on a continuous linear scale and insulin was expressed in quadratic form.

Sensitivity analyses, using a HbA1c cutpoint of 6.0% for exclusion of prevalent diabetes at baseline, were performed in order to check robustness of our models. In addition, although baseline abnormalities in fasting insulin may be considered an intermediary factor in causal pathways, we adjusted for this metabolic parameter in secondary analyses in order to assess the residual predictive role of the inflammatory marker under study. Spearman partial correlation coefficients were calculated for each inflammatory marker against insulin level and against other continuous metabolic variables while controlling for age and BMI.

We used conditional logistic regression to examine the joint role of IL-6 and CRP in predicting diabetes after dividing the primary sample into four groups based on the $75^{th}$ percentile cutpoints for each biomarker. Finally, in order to assess consistency of risk relationships among obese and non-obese individuals, the study sample was divided into six groups based upon a BMI cutpoint value of 29 $kg/m^2$ (the upper tertile of BMI for our study population) and low, medium, and high tertiles of the inflammatory markers.

Results

Baseline characteristics of women who were subsequently diagnosed with diabetes (case subjects) and those remaining free of diabetes (control subjects) are shown in Table 1. As expected, women who subsequently developed diabetes were more obese, more likely to have a family history of diabetes in a first-degree relative, more likely to have a history of hypertension or hyperlipidemia, exercised less frequently, and consumed less alcohol. There were no statistically significant differences in ethnicity, smoking, or hormone replacement therapy use.

Baseline levels of IL-6 and CRP were significantly higher among cases than among controls (Table 1). Moreover, increasing levels of both inflammatory markers were associated with a higher risk of developing future diabetes; in age-matched analyses, the relative risks of incident DM for increasing quartiles of IL-6 were 1.0, 2.5, 4.1, and 7.5 respectively (P-trend<0.001) while the relative risks for increasing quartiles of CRP were 1.0, 2.2, 8.7, and 15.7 respectively (P-trend<0.001) (Tables 2 and 3). BMI adjustment markedly attenuated these relationships, although persistent positive effects of IL-6 (P-trend=0.008) and CRP (P-trend<0.001) were observed. Indeed, CRP remained a significant predictor in fully-adjusted models which included BMI, family history of diabetes, smoking, physical activity, alcohol consumption, and use of hormone replacement therapy. Overall, the relative risk for future diabetes increased 28% (95% CI, −1 to 65 percent; P=0.066) per quartile increase in baseline IL-6 and 64% (95% CI, 22 to 218 percent; P=0.001) per quartile increase in CRP. Similar results were obtained in analyses limited to those with an HbA1c≦6.0% at baseline. For example, in this subset, fully adjusted relative risks of incident diabetes across quartiles of CRP were 1.0, 1.8, 3.8, and 4.9 respectively (P-trend=0.015).

In the subgroup of participants providing fasting specimens, median insulin level was also significantly elevated in case subjects as compared to controls (77.5 versus 39.3 pmol/L, P<0.001). We therefore sought to determine whether relationships between IL-6, CRP, and future risk of DM were independent of fasting insulin. As shown in Table 4, adjustment for baseline fasting insulin further attenuated the effects of IL-6. However, the risk relationship for CRP was not materially altered after adjustment for this factor. In addition, in this subgroup, Spearman partial correlation coefficients between inflammatory markers and both fasting insulin and BMI were statistically significant (Table 5). CRP was more strongly correlated than IL-6 with each parameter tested. Hemoglobin A1c was not strongly associated with either biomarker.

To assess potential joint effects, we computed the relative risk of diabetes mellitus after dividing the original sample into four groups based upon the $75^{th}$ percentile of control distributions for IL-6 and CRP (FIG. 1). As shown, the relative risk of type 2 diabetes was highest among women with both high IL-6 and CRP levels, suggesting a multiplicative effect above that seen for either high IL-6 or high CRP alone.

Figure 2A:
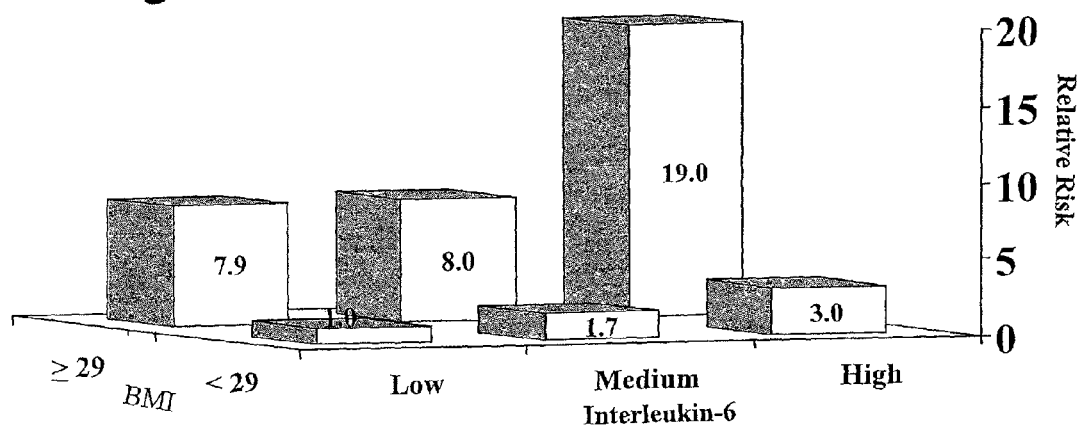
FIG. 2 is a bar graph showing relative risk of diabetes mellitus according to baseline level of IL-6 (FIG. 2A) and CRP (FIG. 2B), and body-mass index (kg/m$^2$).
Figure 2B:
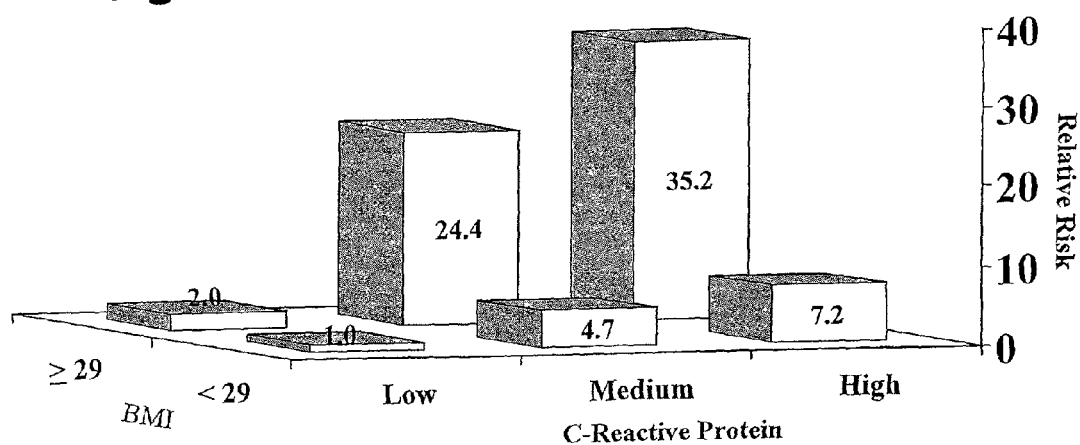

To investigate effect modification by body-mass index, we determined the relative risk of incident diabetes among women with a BMI < or ≧29 $kg/m^2$ (FIG. 2). In both strata, higher baseline plasma levels of IL-6 and CRP were associated with increased risk of incident disease. Notably, even among obese women, increasing CRP levels conferred an augmented stepwise elevation in risk.

Discussion

In this prospective study of apparently healthy middle-aged women, two markers of systemic inflammation, C-reactive protein and interleukin-6, were found to be predictors of risk for future diabetes. In particular, CRP was a powerful independent predictor after adjustment for body-mass index, clinical risk factors, and fasting insulin levels. Parallel associations were found for IL-6, although lower in magnitude and of borderline statistical significance after multivariate adjustments. These findings were robust in sensitivity analyses limited to those with HbA1c≦6.0% and were consistently noted in both non-obese and obese individuals.

To our knowledge, no prior epidemiologic evidence has been available linking baseline CRP and IL-6 to incident diabetes mellitus. Our data also extend prior work in which other inflammatory markers, such as white cell count, fibrinogen, and low serum albumin,[20] and inflammation-associated hemostasis variables, such as Factor VIII and von Willebrand factor,[21] were associated with future risk of diabetes, although in these latter investigations, risk relationships largely disappeared after adjustment for obesity.

The current prospective data support a role of inflammation in diabetogenesis, and are in accord with previous hypotheses originated by Pickup and Crook[8] that type 2 diabetes may be a manifestation of an ongoing cytokine-mediated acute phase response initiated by the body's innate immune system. Of particular relevance to the current findings, C-reactive protein is thought to exhibit several characteristics which imply a fundamental role in natural host defense. Specifically, CRP is a member of the pentraxin family of oligomeric proteins involved with pattern recognition in innate immunity.[22-24] Reported immunoregulatory functions of CRP include enhancement of leukocyte reactivity, complement fixation, modulation of platelet activation, and clearance of cellular debris from sites of active inflammation.[22, 25, 26] In combination, the magnitude and rapidity of CRP induction during acute phase stimuli and cooperative role in the innate immune response suggests the early involvement of C-reactive protein in host defense.[25] With specific regard to the development of type 2 diabetes, endogenous stimulants of the acute phase response, such as obesity, genetic programming, or other constitutional factors, are hypothesized to promote chronic inflammation, eventual insulin resistance and impaired pancreatic beta-cell function.[8] Though our data support etiologic associations, at this time explicit mechanisms remain speculative and require further study.

Several alternative, perhaps coordinate, explanations for our results warrant further discussion. First, it is possible that the associations observed in this study of diabetes reflect underlying atherosclerosis or endothelial dysfunction among case subjects.[13-15, 27-29] In this regard, however, it is worth noting that the four-year cardiovascular event rate among our study population was low (1 case and 1 control with incident stroke, myocardial infarction, coronary angioplasty or bypass surgery), even among those individuals with greatest baseline elevations of either IL-6 or CRP.

Another explanation for the association between elevated inflammatory markers, insulin resistance, and nascent diabetes is related to insulin's effects on hepatic acute phase protein biosynthesis. Insulin has been shown to inhibit the cytokine-driven induction of several inflammatory proteins.[30, 31] It is therefore plausible that insulin resistance may lead to downstream augmentation of CRP production. Indeed, in the present analysis, CRP was found to be significantly correlated with fasting insulin, although the magnitude of this correlation was weak (Spearman partial correlation coefficient, 0.19; P<0.001). Moreover, our finding that control for fasting insulin had minimal influence on primary associations suggests that, although univariate relationships exist, this marker of underlying insulin resistance does not account for the risk attributable to elevated CRP.

Obesity-mediated cytokine production is another important mechanism for endogenous CRP elevation. The primary cytokine involved in hepatic CRP synthesis is interleukin-6, also an important adipocyte signaling molecule released both from visceral and subcutaneous fat stores. Indeed, approximately 25% of in vivo systemic IL-6 originates from subcutaneous adipose tissue[32] and is thought to modify adipocyte glucose and lipid metabolism and body weight.[33-37] Furthermore, omental fat cells have been shown to secrete as much as 2-3 times more IL-6 in vitro than cells derived from subcutaneous stores,[38] an intriguing finding as venous drainage from omental fat provides direct access to the portal system and abdominal adiposity is strongly linked to insulin resistance.[39-42] In the present analysis, body-mass index was used as a measure of obesity, and as expected significantly attenuated relative risk estimates for both IL-6 and CRP. However, highly significant residual effects attributable to CRP were nonetheless observed in multivariate models adjusting for this factor. In addition, a stepwise relative risk gradient was evident even among obese individuals (FIG. 2).

Our cohort was comprised of primarily healthy middle-aged women, and thus our results may not be generalizable to other age groups or to men who may be at risk for type 2 diabetes. In addition, we measured inflammatory biomarkers at study entry and therefore could not evaluate the effects of changes in plasma levels of these biomarkers over time. However, several longitudinal analyses have found that levels of CRP are stable during long-term follow-up, as long as measurements are not made within two weeks of an acute infection.[43, 44]

In conclusion, in this prospective evaluation of two markers of inflammation in the prediction of incident diabetes, CRP was found to be a powerful risk determinant. Interleukin-6 was also elevated among individuals at risk, although these associations were attenuated in multivariate analyses. Our epidemiologic observations, coupled with emerging experimental evidence, support a role for inflammation in the pathogenesis of type 2 diabetes mellitus. Our data also raise the possibility that inflammatory markers, like CRP, might provide an adjunctive method for early detection of risk for this disease.

REFERENCES

1. Harris M. Diabetes in America: diabetes data compiled 1995. In: Group NDD, ed. U.S. Department of Health and Human Services publication (PHS) 95-1468. Vol. VI 1-31.32: National Institutes of Health, 1995:1-13.
2. Harris M I, Flegal K M, Cowie C C, et al. Prevalence of diabetes, impaired fasting glucose, and impaired glucose tolerance in U.S. adults. The Third National Health and Nutrition Examination Survey, 1988-1994 [see comments]. Diabetes Care 1998; 21:518-24.
3. Manson J, A S. Risk modification in the diabetic patient. In: Manson J, Ridker P, Gaziano J, Hennekens C, eds. Prevention of Myocardial Infarction. New York: Oxford University Press, 1996:241-273.
4. Harris M I, Klein R, Welborn T A, Knuiman M W. Onset of NIDDM occurs at least 4-7 yr before clinical diagnosis. Diabetes Care 1992; 15:815-9.
5. Reaven G M. Banting lecture 1988. Role of insulin resistance in human disease. Diabetes 1988; 37:1595-607.
6. DeFronzo R A. Lilly lecture 1987. The triumvirate: beta-cell, muscle, liver. A collusion responsible for NIDDM. Diabetes 1988; 37:667-87.
7. Bergman R N. Lilly lecture 1989. Toward physiological understanding of glucose tolerance. Minimal-model approach. Diabetes 1989; 38:1512-27.
8. Pickup J C, Crook M A. Is type II diabetes mellitus a disease of the innate immune system? [see comments]. Diabetologia 1998; 41:1241-8.
9. Pickup J C, Mattock M B, Chusney G D, Burt D. NIDDM as a disease of the innate immune system: association of acute-phase reactants and interleukin-6 with metabolic syndrome X. Diabetologia 1997; 40:1286-92.
10. Hak A E, Stehouwer C D, Bots M L, et al. Associations of C-reactive protein with measures of obesity, insulin resistance, and subclinical atherosclerosis in healthy, middle-aged women. Arterioscler Thromb Vasc Biol 1999; 19:1986-91.
11. Yudkin J S, Stehouwer C D, Emeis J J, Coppack S W. C-reactive protein in healthy subjects: associations with obesity, insulin resistance, and endothelial dysfunction: a potential role for cytokines originating from adipose tissue? Arterioscler Thromb Vasc Biol 1999; 19:972-8.
12. Festa A, D'Agostino R, Jr., Howard G, Mykkanen L, Tracy R P, Haffner S M. Chronic subclinical inflammation as part of the insulin resistance syndrome: the Insulin Resistance Atherosclerosis Study (IRAS). Circulation 2000; 102:42-7.
13. Ridker P M, Cushman M, Stampfer M J, Tracy R P, Hennekens C H. Inflammation, aspirin, and the risk of cardiovascular disease in apparently healthy men [published erratum appears in N Engl J Med 1997 Jul. 31;337 (5):356] [see comments]. N Engl J Med 1997; 336:973-9.
14. Ridker P M, Hennekens C H, Buring J E, Rifai N. C-reactive protein and other markers of inflammation in the prediction of cardiovascular disease in women. N Engl J Med 2000; 342:836-43.
15. Ridker P M, Rifai N, Stampfer M J, Hennekens C H. Plasma concentration of interleukin-6 and the risk of future myocardial infarction among apparently healthy men. Circulation 2000; 101:1767-72.
16. Buring J, Hennekens C. The Women's Health Study: summary of the study design. J Myocard Ischemia 1992; 4:27-29.
17. Report of the Expert Committee on the Diagnosis and Classification of Diabetes Mellitus [see comments]. Diabetes Care 1997; 20:1183-97.
18. Rifai N, Tracy R P, Ridker P M. Clinical efficacy of an automated high-sensitivity C-reactive protein assay. Clin Chem 1999; 45:2136-41.
19. Chevenne D, Trivin F, Porquet D. Insulin assays and reference values. Diabetes Metab 1999; 25:459-76.
20. Schmidt M I, Duncan B B, Sharrett A R, et al. Markers of inflammation and prediction of diabetes mellitus in adults (Atherosclerosis Risk in Communities study): a cohort study. Lancet 1999; 353:1649-52.
21. Duncan B B, Schmidt M I, Offenbacher S, Wu K K, Savage P J, Heiss G. Factor VIII and other hemostasis variables are related to incident diabetes in adults. The Atherosclerosis Risk in Communities (ARIC) Study. Diabetes Care 1999; 22:767-72.
22. Gewurz H, Zhang X H, Lint T F. Structure and function of the pentraxins. Curr Opin Immunol 1995; 7:54-64.
23. Fearon D T, Locksley R M. The instructive role of innate immunity in the acquired immune response. Science 1996; 272:50-3.
24. Medzhitov R, Janeway C A, Jr. Innate immunity: impact on the adaptive immune response. Curr Opin Immunol 1997; 9:4-9.
25. Steel D M, Whitehead A S. The major acute phase reactants: C-reactive protein, serum amyloid P component and serum amyloid A protein. Immunol Today 1994; 15:81-8.
26. Mortensen R. Macrophages and Acute-Phase Proteins. In: Zwilling B, Eisenstein T, eds. Macrophage-Pathogen Interactions. New York: Marcel Deckker, 1994:143-158.
27. Danesh J, Whincup P, Walker M, et al. Low grade inflammation and coronary heart disease: prospective study and updated meta-analyses [see comments]. BMJ 2000; 321: 199-204.
28. Fichtlscherer S, Rosenberger G, Walter D H, Breuer S, Dimmeler S, Zeiher A M. Elevated C-reactive protein levels and impaired endothelial vasoreactivity in patients with coronary artery disease. Circulation 2000; 102:1000-6.
29. Hingorani A D, Cross J, Kharbanda R K, et al. Acute systemic inflammation impairs endothelium-dependent dilatation in humans. Circulation 2000; 102:994-9.
30. Thompson D, Harrison S P, Evans S W, Whicher J T. Insulin modulation of acute-phase protein production in a human hepatoma cell line. Cytokine 1991; 3:619-26.
31. Campos S P, Baumann H. Insulin is a prominent modulator of the cytokine-stimulated expression of acute-phase plasma protein genes. Mol Cell Biol 1992; 12:1789-97.
32. Mohamed-Ali V, Goodrick S, Rawesh A, et al. Subcutaneous adipose tissue releases interleukin-6, but not tumor necrosis factor-alpha, in vivo. J Clin Endocrinol Metab 1997; 82:4196-200.
33. Sandier S, K Kb, DL E, M W. Interleukin-6 affects insulin secretion and glucose metabolism of rat pancreatic islets in vitro. Endocrinology 1990; 126:1288-1294.
34. Stith R, J L. Endocrine and carbohydrate responses to interleukin-6 in vivo. Circulatory Shock 1994; 44:210-215.
35. Greenberg A S, Nordan R P, McIntosh J, Calvo J C, Scow R O, Jablons D. Interleukin 6 reduces lipoprotein lipase activity in adipose tissue of mice in vivo and in 3T3-L1 adipocytes: a possible role for interleukin 6 in cancer cachexia. Cancer Res 1992; 52:4113-6.
36. Berg M, Fraker D L, Alexander H R. Characterization of differentiation factor/leukaemia inhibitory factor effect on lipoprotein lipase activity and mRNA in 3T3-L1 adipocytes. Cytokine 1994; 6:425-32.
37. Orban Z, Remaley A T, Sampson M, Trajanoski Z, Chrousos G P. The differential effect of food intake and beta-adrenergic stimulation on adipose-derived hormones and cytokines in man. J Clin Endocrinol Metab 1999; 84:2126-33.
38. Fried S K, Bunkin D A, Greenberg A S. Omental and subcutaneous adipose tissues of obese subjects release interleukin-6: depot difference and regulation by glucocorticoid. J Clin Endocrinol Metab 1998; 83:847-50.
39. Despres J P. Abdominal obesity as important component of insulin-resistance syndrome. Nutrition 1993; 9:452-9.
40. Carey D G, Jenkins A B, Campbell L V, Freund J, Chisholm D J. Abdominal fat and insulin resistance in normal and overweight women: Direct measurements reveal a strong relationship in subjects at both low and high risk of NIDDM. Diabetes 1996; 45:633-8.
41. Vanhala M J, Pitkajarvi T K, Kumpusalo E A, Takala J K. Obesity type and clustering of insulin resistance-associated cardiovascular risk factors in middle-aged men and women. Int J Obes Relat Metab Disord 1998; 22:369-74.
42. Brochu M, Starling R D, Tchernof A, Matthews D E, Garcia-Rubi E, Poehlman E T. Visceral adipose tissue is an independent correlate of glucose disposal in older obese postmenopausal women. J Clin Endocrinol Metab 2000; 85:2378-84.
43. Ridker P M, Rifai N, Pfeffer M A, Sacks F, Braunwald E. Long-term effects of pravastatin on plasma concentration of C-reactive protein. The Cholesterol and Recurrent Events (CARE) Investigators. Circulation 1999; 100:230-5.
44. Ockene I, Matthews C, Rifai N, Ridker P, Reed G, Stanek E. Variability and classification accuracy of serial high-sensitivity C-reactive protein measurements in healthy adults. Clin Chem. 2001;47(3):444-50.

TABLE 1

Baseline Characteristics of the Study Population[554]

| Characteristic | Cases (N = 188) | Controls (N = 362) | P-value |
|---|---|---|---|
| Mean Age | 54.7 | 54.7 | — |
| Mean Body-Mass Index[555] | 31.8 | 25.6 | <0.001 |
| Race (%) | | | |
| White | 90.4 | 91.7 | 0.61 |
| Non-White/Unknown | 9.6 | 8.3 | |
| Family History of Diabetes (%) | 44.2 | 23.8 | <0.001 |

TABLE 1-continued

Baseline Characteristics of the Study Population[554]

| Characteristic | Cases (N = 188) | Controls (N = 362) | P-value |
|---|---|---|---|
| History of Hypertension (%) | 58.5 | 24.6 | <0.001 |
| History of Hyperlipidemia (%) | 43.6 | 27.9 | <0.001 |
| Smoking Status (%) | | | |
| Non-smoker | 51.6 | 51.1 | |
| Former smoker | 35.6 | 37.3 | 0.89 |
| Current smoker | 12.8 | 11.6 | |
| Frequency of Exercise (%) | | | |
| Rarely or never | 43.6 | 33.4 | |
| <1 time/week | 26.1 | 18.2 | <0.001 |
| 1-3 times/week | 25.0 | 34.8 | |
| ≧4 times/week | 5.3 | 13.5 | |
| Frequency of Alcohol Consumption (%) | | | |
| Rarely or never | 61.7 | 39.8 | |
| Monthly | 14.9 | 14.4 | <0.001 |
| Weekly | 21.3 | 34.5 | |
| Daily | 2.1 | 11.3 | |
| Hormone Replacement Therapy Use (%) | | | |
| Never | 43.1 | 45.0 | 0.28 |
| Past Only | 13.8 | 9.4 | |
| Current | 43.1 | 45.6 | |
| Interleukin-6 (pg/ml) | | | |
| Median | 2.00 | 1.38 | <0.001 |
| Interquartile Range | 1.43-2.78 | 0.91-2.05 | |
| C-reactive Protein (mg/dl) | | | |
| Median | 0.69 | 0.26 | <0.001 |
| Interquartile Range | 0.42-1.00 | 0.10-0.61 | |

[†]Restricted to subjects with HbA1c ≦ 6.5% at baseline, N = 550.
[‡]The body-mass index is the weight in kilograms divided by the square of the height in meters.

TABLE 2

Crude and Adjusted Relative Risks of Diabetes According to Baseline Plasma Concentration of IL-6[†]

| | Quartile of IL-6 Median (pg/ml) (Range pg/ml) | | | | |
|---|---|---|---|---|---|
| | 1 0.698 (<0.909) | 2 1.133 (0.91-1.382) | 3 1.646 (1.383-2.050) | 4 2.709 (>2.050) | P-trend |
| Crude Analysis | | | | | |
| Relative Risk | 1.0 | 2.5 | 4.1 | 7.5 | <0.001 |
| 95% CI | | (1.1-5.6) | (2.0-8.4) | (3.7-15.4) | |
| P | | 0.022 | <0.001 | <0.001 | |
| BMI[‡] Adjusted Analysis | | | | | |
| Relative Risk | 1.0 | 1.8 | 1.9 | 2.9 | 0.008 |
| 95% CI | | (0.7-4.4) | (0.8-4.2) | (1.3-6.7) | |
| P | | 0.19 | 0.12 | 0.010 | |
| Adjusted for All Risk Factors[¥] | | | | | |
| Relative Risk | 1.0 | 1.4 | 1.3 | 2.3 | 0.066 |
| 95% CI | | (0.6-3.7) | (0.6-3.1) | (0.9-5.6) | |
| P | | 0.47 | 0.51 | 0.08 | |

[†]Restricted to subjects with HbA1c < 6.5% at baseline.
[‡]BMI denotes body-mass index.
[¥]Matched on age and fasting status, controlled for body-mass index, family history of diabetes, smoking, physical activity, alcohol consumption, and hormone replacement therapy.

TABLE 3

Crude and Adjusted Relative Risks of Diabetes According to Baseline Plasma Concentration of C-Reactive Protein[554]

| | Quartile of C-Reactive Protein Median (mg/dl) (Range mg/dl) | | | | |
|---|---|---|---|---|---|
| | 1 0.050 (<0.10) | 2 0.170 (0.10-0.26) | 4 0.435 (0.27-0.61) | 4 0.930 (>0.61) | P-trend |
| Crude Analysis | | | | | |
| Relative Risk | 1.0 | 2.2 | 8.7 | 15.7 | <0.001 |
| 95% CI | | (0.8-6.0) | (3.6-21.0) | (6.5-37.9) | |
| P | | 0.13 | <0.001 | <0.001 | |

TABLE 3-continued

Crude and Adjusted Relative Risks of Diabetes
According to Baseline Plasma Concentration of C-Reactive Protein[554]

| | Quartile of C-Reactive Protein Median (mg/dl) (Range mg/dl) | | | | |
|---|---|---|---|---|---|
| | 1<br>0.050<br>(<0.10) | 2<br>0.170<br>(0.10-0.26) | 4<br>0.435<br>(0.27-0.61) | 4<br>0.930<br>(>0.61) | P-trend |
| BMI[‡] Adjusted Analysis | | | | | |
| Relative Risk | 1.0 | 1.2 | 4.1 | 4.4 | <0.001 |
| 95% CI | | (0.4-3.5) | (1.6-10.6) | (1.7-11.5) | |
| P | | 0.73 | 0.004 | 0.002 | |
| Adjusted for All Risk Factors[¥] | | | | | |
| Relative Risk | 1.0 | 1.3 | 4.1 | 4.2 | 0.001 |
| 95% CI | | (0.4-4.1) | (1.5-11.5) | (1.5-12.0) | |
| P | | 0.61 | 0.007 | 0.007 | |

[†]Restricted to subjects with HbA1c ≦ 6.5% at baseline.
[‡]BMI denotes body-mass index.
[¥]Matched on age and fasting status, controlled for body-mass index, family history of diabetes, smoking, physical activity, alcohol consumption, and hormone replacement therapy.

TABLE 4

Adjusted Relative Risks of Diabetes According to Baseline Plasma
Concentration of C-Reactive Protein and Interleukin-6
Adjusted for Fasting Plasma Insulin in Addition to Clinical Parameters[554]

| | Quartile of Plasma Biomarker Level | | | | |
|---|---|---|---|---|---|
| | 1 | 2 | 3 | 4 | P-Trend |
| Interleukin-6<br>Adjusted for Fasting Insulin<br>Plus Clinical Parameters[‡] | | | | | |
| Relative Risk | 1.0 | 0.7 | 0.9 | 1.5 | 0.23 |
| 95% CI | | (0.2-2.6) | (0.3-2.9) | (0.5-4.8) | |
| P | | 0.56 | 0.89 | 0.51 | |
| C-Reactive Protein<br>Adjusted for Fasting Insulin<br>Plus Clinical Parameters[‡] | | | | | |
| Relative Risk | 1.0 | 0.9 | 3.1 | 4.3 | 0.010 |
| 95% CI | | (0.2-4.3) | (0.8-12.2) | (1.1-17.1) | |
| P | | 0.91 | 0.10 | 0.040 | |

[†]Restricted to subjects with HbA1c ≦ 6.5% at baseline; 126 cases, 225 controls.
[‡]Matched on age and fasting status, controlled for body-mass index, family history of diabetes, smoking, physical activity, alcohol consumption and hormone replacement therapy.

TABLE 5

Spearman Partial Correlation Coefficients of Inflammatory
Markers with Body-Mass Index (BMI) and
Metabolic Parameters[†]

| | BMI[¥] | HbA1c[§] | Fasting Insulins[§] | IL-6[§] | CRP[§] |
|---|---|---|---|---|---|
| Interleukin-6 | 0.45[‡] | 0.07 | 0.18[555] | — | 0.39[‡] |
| C-Reactive Protein | 0.57[‡] | 0.10 | 0.19[‡] | 0.39[‡] | — |

[†]Limited to subjects with HbA1c ≦ 6.5% at baseline and providing fasting blood specimens; 126 cases, 225 controls.
[¥]Adjusted for age.
[§]Adjusted for age and BMI.
[‡]p-value < 0.001

Example 2

To determine whether elevated levels of C-reactive protein (CRP) and interleukin-6 (IL-6) are independently associated with fasting insulin levels among non-diabetic women, a second study was performed. In this study, 349 healthy, non-diabetic, women aged 45 years and older who provided fasting blood specimens and were free from clinically diagnosed type 2 diabetes mellitus during a period of 4 years from initial biomarker assessment.

Results

Fasting insulin was strongly associated with body mass index (BMI) ($r=0.53$, $p<0.001$), CRP ($r=0.38$, $p<0.001$), and IL-6 ($r=0.33$, $p<0.001$). Other clinical correlates of fasting insulin included level of physical activity, alcohol consumption, and use of hormone replacement therapy. In multivariable linear regression models, BMI and CRP were the only significant independent predictors of log-normalized fasting insulin. Overall, the final model explained 32% of the variance in log insulin level. In multivariable logistic regression, the fully adjusted odds ratio (OR) for elevated fasting insulin ($\geqq 51.6$ pmol/L) increased with increasing tertile of BMI, CRP, and IL-6 such that the ORs in the highest versus lowest tertile of each parameter were 9.0 (95% CI 4.4-18.7), 4.4

(95% CI 1.9-10.1), and 2.0 (95% CI 0.9-4.2), respectively. Furthermore, increasing levels of CRP were associated with a stepwise gradient in odds for elevated fasting insulin among both lean and overweight women. Thus, C-reactive protein is independently associated with fasting hyperinsulinemia in non-diabetic women.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is presented below.

We claim:

1. A method for predicting an individual's risk profile of developing future diabetes or a diabetic complication, comprising:
    selecting an individual who is free of diabetes,
    obtaining a level of C-reactive protein in a blood sample from the individual,
    comparing the level of C-reactive protein in the blood sample from the individual to a predetermined value of 0.30 mg/dl, and if said level of C-reactive protein is about 0.30 mg/dl or higher in the blood sample from the individual, then
    predicting said individual as having an increased risk of developing future diabetes or a diabetic complication, wherein the diabetic complication is diabetic ketoacidosis, hyperosmolar coma, retinopathy, diabetic nephropathy, diabetic neuropathy, or diabetic foot ulcers.

2. The method of claim 1, wherein the level of C-reactive protein is about 0.60 mg/dl or higher in the blood sample from the individual.

3. A method for predicting an individual's risk profile of developing future diabetes or a diabetic complication, comprising:
    selecting an individual who is free of diabetes,
    obtaining a level of C-reactive protein in a blood sample from the individual, wherein a level of C-reactive protein about 0.30 mg/dl or higher in the blood sample from the individual establishes a first risk value,
    obtaining a level of a glycosylated hemoglobin in a blood sample from the individual,
    comparing the level of the glycosylated hemoglobin to a second predetermined value specific for the diagnosis of diabetes or a diabetic complication to establish a second risk value, and
    predicting the individual's risk profile of developing diabetes or a diabetic complication based upon the combination of the first risk value and the second risk value, wherein the combination of the first risk value and second risk value establishes a third risk value different from said first and second risk values.

4. The method of claim 3, wherein the level of C-reactive protein is about 0.60 mg/dl or higher in the blood sample of the individual.

5. A method for evaluating the likelihood that an individual will benefit from treatment with an agent for reducing the risk of diabetes, wherein the agent is insulin, a hypoglycemic agent, an anti-inflammatory agent, a lipid lowering agent, a calcium channel blocker, a beta-adrenergic receptor blocker, a cyclooxygenase-2 inhibitor, or an angiotensin system inhibitor, comprising:
    selecting an individual who is free of diabetes,
    obtaining a level of C-reactive protein in a blood sample from the individual,
    comparing the level of C-reactive protein in the blood sample from the individual to a predetermined value of 0.30 mg/dl, and if said level of C-reactive protein is about 0.30 mg/dl or higher in the blood sample from the individual, then
    predicting said individual as likely to benefit from treatment with said agents, wherein the lipid lowering agent is not an HMG-CoA reductase inhibitor.

6. The method of claim 5, wherein the agent is a hypoglycemic agent.

7. The method of claim 5, wherein the level of C-reactive protein is about 0.60 mg/dL or higher in the blood sample from the individual.

8. The method of claim 5, wherein the agent is insulin.

9. The method of claim 5, wherein the agent is an anti-inflammatory agent.

10. The method of claim 5, wherein the agent is a lipid lowering agent.

11. The method of claim 5, wherein the agent is a calcium channel blocker.

12. The method of claim 5, wherein the agent is a beta-adrenergic receptor blocker.

13. The method of claim 5, wherein the agent is a cyclooxygenase-2 inhibitor.

14. The method of claim 5, wherein the agent is an angiotensin system inhibitor.

15. The method of claim 1, wherein the diabetes or a diabetic complication is diabetes.

16. The method of claim 1, wherein the diabetes or a diabetic complication is a diabetic complication.

17. The method of claim 3, wherein the diabetes or a diabetic complication is diabetes.

18. The method of claim 3, wherein the diabetes or a diabetic complication is a diabetic complication.

19. The method of claim 5, wherein the agent is an agent for reducing the risk of diabetes.

* * * * *